US009956324B2

(12) United States Patent
Anzai et al.

(10) Patent No.: US 9,956,324 B2
(45) Date of Patent: May 1, 2018

(54) MEDICAL MATERIAL, AND MEDICAL DEVICE USING THE MEDICAL MATERIAL (71) Applicant: TERUMO KABUSHIKI KAISHA, Shibuya-ku (JP)

(72) Inventors: Takao Anzai, Hiratsuka (JP); Kaori Nishida, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days. days.

(21) Appl. No.: 15/244,506

(22) Filed: Aug. 23, 2016

(65) Prior Publication Data
US 2017/0128636 A1    May 11, 2017

Related U.S. Application Data (63) Continuation of application No. PCT/JP2015/054674, filed on Feb. 19, 2015.

(30) Foreign Application Priority Data

Feb. 24, 2014 (JP) .................. 2014-033404

(51) Int. Cl.
| A61L 31/00 | (2006.01) |
| A61L 33/06 | (2006.01) |
| A61L 27/34 | (2006.01) |
| A61L 31/10 | (2006.01) |
| C08F 222/28 | (2006.01) |
| C09D 133/14 | (2006.01) |
| C08F 220/28 | (2006.01) |

(52) U.S. Cl.
CPC .......... *A61L 33/068* (2013.01); *C08F 220/28* (2013.01); *A61L 2300/42* (2013.01); *A61L 2420/00* (2013.01); *C08F 2220/281* (2013.01)

(58) Field of Classification Search
None
See application file for complete search history.

(56) References Cited

U.S. PATENT DOCUMENTS 6,133,391 A * 10/2000 Nielson ............... C08F 220/18
                                                       206/524
8,263,720 B1 * 9/2012 Salamone ........... A61L 26/0019
                                                       424/443
(Continued)

FOREIGN PATENT DOCUMENTS

| JP | 4-152952 A | 5/1992 |
| JP | 11-114056 A | 4/1999 |

(Continued)

OTHER PUBLICATIONS

International Search Report (PCT/ISA/210) dated May 19, 2015, by the Japanese Patent Office as the International Searching Authority for International Application No. PCT/JP2015/054674.

Venault et al., Surface self-assembled zwitterionization of poly (vinylidene fluoride) microfiltration membranes via hydrophobic-driven coating for improved blood compatibility, J. Membrane Science, Dec. 18, 2013, vol. 454, pp. 253-263.

(Continued)

*Primary Examiner* — Abigail Vanhorn
(74) *Attorney, Agent, or Firm* — Buchanan Ingersoll & Rooney PC (57) ABSTRACT

The disclosure relates to a medical material including a copolymer having a repeating unit (A) represented by the following formula (1):

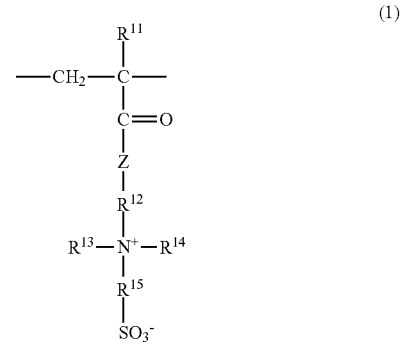

wherein $R^{11}$ is a hydrogen atom or a methyl group, Z is an oxygen atom or —NH—, $R^{12}$ is a $C_{1-6}$ alkylene group, $R^{13}$ and $R^{14}$ are each independently a $C_{1-4}$ alkyl group, and $R^{15}$ is a $C_{1-6}$ alkylene group, and a repeating unit (B) represented by the following formula (2):

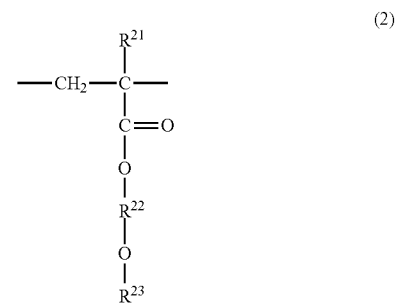

wherein $R^{21}$ is a hydrogen atom or a methyl group, $R^{22}$ is a $C_{1-6}$ alkylene group, and $R^{23}$ is a $C_{1-4}$ alkyl group. The repeating unit (A) is contained in a proportion of 0.6 to 7 mol % based on all the structural units of the copolymer. The disclosure makes it possible to provide a medical material and a medical device, which exhibit excellent antithrombogenicity even when used under severe conditions prone to thrombus formation.

17 Claims, 4 Drawing Sheets

(56) References Cited

U.S. PATENT DOCUMENTS

| | | |
|---|---|---|
| 2002/0064558 A1 | 5/2002 | Tanaka et al. |
| 2008/0262181 A1 | 10/2008 | Kitano et al. |
| 2010/0152402 A1 | 6/2010 | Pacetti et al. |
| 2011/0305872 A1 | 12/2011 | Li et al. |
| 2011/0305898 A1 | 12/2011 | Zhang et al. |
| 2013/0158488 A1 | 6/2013 | Weaver et al. |
| 2013/0158518 A1 | 6/2013 | Li et al. |
| 2013/0323291 A1 | 12/2013 | Li et al. |
| 2016/0122488 A1 | 5/2016 | Minagawa |

FOREIGN PATENT DOCUMENTS

| | | |
|---|---|---|
| JP | 2002-105136 A | 4/2002 |
| JP | 2009-219936 A | 10/2009 |
| JP | 2013/528114 A | 7/2013 |
| JP | 2014-147638 A | 8/2014 |
| WO | WO 2005/113620 A1 | 12/2005 |
| WO | WO 2011/156589 A1 | 12/2011 |
| WO | WO 2011/156590 A2 | 12/2011 |
| WO | WO 2013/090693 A1 | 6/2013 |
| WO | WO 2013/090695 | 6/2013 |
| WO | WO 2013/180940 | 12/2013 |
| WO | WO 2014/203668 A1 | 12/2014 |

OTHER PUBLICATIONS

Yuan et al., Polyurethane vascular catheter surface grafted with zwitterionic sulfobetaine monomer activated by ozone, Colloids Surf. B: Biointerfaces, 2004 (month unknown), vol. 35, No. 1, pp. 1-5.

Extended Search Report issued by the European Patent Office in corresponding European Patent Application No. 15752648.4 dated Sep. 20, 2017 (6 pages).

* cited by examiner

MEDICAL MATERIAL, AND MEDICAL DEVICE USING THE MEDICAL MATERIAL

CROSS-REFERENCES TO RELATED APPLICATIONS

This application is a continuation of International Application No. PCT/JP2015/054674 filed on Feb. 19, 2015, and claims priority to Japanese Patent Application No. 2014-033404 filed on Feb. 24, 2014, the entire content of both of which is incorporated herein by reference.

TECHNICAL FIELD

The present disclosure relates to a medical material and also to a medical device using the medical material. More specifically, the present disclosure relates to a medical material containing a copolymer having specific repeating units and also to a medical device using the medical material.

BACKGROUND DISCUSSION

In recent years, medical materials utilizing various polymer materials have been studied, and they are expected to be used for membranes for artificial kidneys, membranes for plasma skimming, catheters, stents, membranes for artificial lungs, artificial blood vessels, anti-adhesion membranes, artificial skins, and the like. In these materials, a synthetic polymer material, which is an xenobiotic substance, is used in contact with a biological tissue or a body fluid such as blood. Therefore, such a medical material is required to be biocompatible. The biocompatibility required for a medical material varies depending on its purpose and usage. A medical material used as a material that contacts blood is required to have characteristics of inhibiting the blood coagulation system, inhibiting the adhesion/activation of platelets, and inhibiting the activation of the complement system (antithrombogenicity).

Usually, a medical device is made antithrombogenic by a method in which the substrate forming the medical device is covered with an antithrombogenic material, or a method in which an antithrombogenic material is fixed to the surface of the substrate.

For example, JP-A-4-152952 discloses a membrane for an artificial organ or a medical device, having on the surface thereof a synthetic polymer that simultaneously satisfies biocompatibilities of inhibiting the adhesion/activation of platelets, an inhibitory effect on the activation of the complement system, and affinity with in-vivo tissues. In addition, U.S. Patent Application No. 2008/0262181 (corresponding to WO 2005/113620) discloses a biocompatible material containing a homopolymer or copolymer that has reduced interaction with biological components such as proteins and blood cells and is highly biocompatible.

SUMMARY

The invention disclosed in JP-A-4-152952 shows excellent results in terms of inhibiting the adhesion/activation of platelets. In addition, according to the invention disclosed in U.S. Patent Application No. 2008/0262181, the biocompatible material is excellent in terms of inhibiting the adsorption of proteins.

However, when a medical device has a step(s) on the surface thereof that contacts blood, the blood flow is impaired at the step(s), resulting in a tendency that thrombus formation is likely to occur around the steps. The term "step" refers to the configuration that results when one member is applied on another member and a gap exists between the inner surface of the one member and the inner surface of the other member. For example, in a blood flow circuit of a medical device, the blood flow is likely to be impaired around a constricted portion such as the joint of tubes used for the medical device, whereby thrombus formation is relatively likely to occur. Then, under such severe conditions relatively prone to thrombus formation, the materials according to the inventions disclosed in JP-A-4-152952 and U.S. Patent Application No. 2008/0262181 have been sometimes insufficient in terms of antithrombogenicity.

Thus, the present disclosure has been accomplished against the above background. Disclosed here is a medical material and a medical device, which particularly exhibit excellent antithrombogenicity even when used under severe conditions prone to thrombus formation.

The present inventors have conducted extensive research to solve the aforementioned problems. As a result, they have found that the problems may be solved by a medical material containing a copolymer having specific repeating units, in which the content ratios of the specific repeating units are within specific ranges.

That is, the gist of the present disclosure is as follows.

1. A medical material including a copolymer comprising:
a repeating unit (A) represented by the following formula (1):

[Chemical Formula 1]

wherein $R^{11}$ is a hydrogen atom or a methyl group, Z is an oxygen atom or —NH—, $R^{12}$ is a $C_{1-6}$ alkylene group, $R^{13}$ and $R^{14}$ are each independently a $C_{1-4}$ alkyl group, and $R^{15}$ is a $C_{1-6}$ alkylene group; and a repeating unit (B) represented by the following formula (2):

[Chemical Formula 2]

wherein $R^{21}$ is a hydrogen atom or a methyl group, $R^{22}$ is a $C_{1-6}$ alkylene group, and $R^{23}$ is a $C_{1-4}$ alkyl group, the repeating unit (A) being contained in a proportion of 0.6 to 7 mol % based on all the structural units of the copolymer;

2. The medical material according to 1 above, wherein in the formula (2), $R^{21}$ is a hydrogen atom or a methyl group, $R^{22}$ is a $C_{1-3}$ alkylene group, and $R^{23}$ is a $C_{1-2}$ alkyl group;

3. The medical material according to 1 or 2 above, wherein in the formula (1), $R^{11}$ is a methyl group, Z is an oxygen atom or —NH—, $R^{12}$ is a $C_{1-4}$ alkylene group, $R^{13}$ and $R^{14}$ are each independently a $C_{1-2}$ alkyl group, and $R^{15}$ is a $C_{1-4}$ alkylene group;

4. The medical material according to any one of 1 to 3 above, wherein the copolymer includes 0.6 to 7 mol % the repeating unit (A) and 99.4 to 93 mol % the repeating unit (B) (the total amount of the repeating unit (A) and the repeating unit (B) is 100 mol %);

5. A medical device comprising:
a substrate; and,
on a surface of the substrate, a coating layer containing the medical material according to any one of 1 to 4 above.

BRIEF DESCRIPTION OF DRAWINGS

In FIG. 1, the circled portions each show the joint between tubes 1 and 2.

DETAILED DESCRIPTION

The present disclosure relates to a medical material containing a copolymer having specific repeating units and also to a medical device using the medical material.

The description below describes embodiments of a medical material and a medical device using the medical material representing examples of the inventive medical material and medical device disclosed here. The present disclosure is not limited only to the following embodiments. In addition, the scale ratio in the drawings is exaggerated for the convenience of explanation, and may be different from the actual ratio.

In addition, as used herein, "X to Y" indicating a range means "X or more and Y or less", and "weight", "wt %", and "part by weight" are treated as synonymous with "mass", "mass %", and "part by mass", respectively. In addition, unless otherwise noted, the operations, physical properties, and the like are measured under the condition of room temperature (20 to 25° C.) and a relative humidity of 40 to 50%.

According to an embodiment disclosed here, provided is a medical material including a copolymer comprising:
a repeating unit (A) represented by the following formula (3):

[Chemical Formula 3]

(3)

wherein $R^{11}$ is a hydrogen atom or a methyl group, Z is an oxygen atom or —NH—, $R^{12}$ is a $C_{1-6}$ alkylene group, $R^{13}$ and $R^{14}$ are each independently a $C_{1-4}$ alkyl group, and $R^{15}$ is a $C_{1-6}$ alkylene group; and
a repeating unit (B) represented by the following formula (4):

[Chemical Formula 4]

(4)

wherein $R^{21}$ is a hydrogen atom or a methyl group, $R^{22}$ is a $C_{1-6}$ alkylene group, and $R^{23}$ is a $C_{1-4}$ alkyl group, the repeating unit (A) being contained in a proportion of 0.6 to 7 mol % based on the total structural units of the copolymer.

[Medical Material]

Hereinafter, first, the medical material according to an embodiment of the present disclosure will be described in detail.

The medical material of the present disclosure may be characterized in that it comprises a copolymer having a repeating unit (A) represented by the above formula (1) (hereinafter also simply referred to as "repeating unit (A)") and a repeating unit (B) represented by the above formula (2) (hereinafter also simply referred to as "repeating unit (B)"), and the copolymer contains the repeating unit (A) in a proportion of 0.6 to 7 mol % based on all the structural units.

The present inventors have found that when the repeating unit (A) is combined with the repeating unit (B), and a coating layer is formed using a copolymer containing these repeating units, a medical material (antithrombogenic material) having excellent antithrombogenicity may be obtained.

JP-A-4-152952 discloses a biocompatible biomedical material composed of a homopolymer of the repeating unit (B) or a copolymer containing the same. However, as described above, there has been a demand for further improvement in antithrombogenicity under conditions prone to thrombus formation. Then, in order to achieve further improvement in antithrombogenicity, the present inventors have studied structural units to be contained in a copolymer together with the repeating unit (B). In the course of study, they have found that, surprisingly, when the copolymer comprises, as a repeating unit, an apparently nonionic zwitterion-containing backbone such as a sulfobetaine backbone, the antithrombogenicity may be improved. Without wishing to be bound by any particular theory, it is believed that the improvement in antithrombogenicity appears to be attributable to the following: when a repeating unit (A) having high hydrophilicity is contained in the copolymer, the hydrophilicity of the copolymer is moderately controlled, and the biocompatibility is enhanced, resulting in a significantly improved inhibitory effect on thrombus formation. In addition, it has been found that when the copolymer contains, among a number of zwitterions, a zwitterion moiety with a sulfobetaine backbone, such a copolymer exhibits particularly excellent antithrombogenicity. Without wishing to be bound by any particular theory, it is believed that this may be attributable to the following: when a polymer prepared by copolymerizing a sulfobetaine with an alkoxy acrylate is present on a surface, the surface hydration structure may be closer to a biological component than in the case of a carboxybetaine, whereby xenorecognition reactions are reduced, resulting in excellent antithrombogenicity. Therefore, as compared with the copolymer having a carboxybetaine backbone disclosed in U.S. Patent Application No. 2008/0262181, the medical material of the present disclosure appears to be even more effective in improving antithrombogenicity.

However, as a result of further study of copolymers comprising the repeating units (A) and (B), it has turned out that when the content ratio of the repeating unit (A) is increased, although the antithrombogenicity is improved, the water solubility becomes too high. When a coating layer is formed using such a copolymer having extremely high water solubility on the substrate of a medical device, at the time of using the medical device or the like, the medical material comprising the copolymer may be eluted upon contact with a body fluid such as blood. In particular, in a blood flow circuit such as an artificial lung system, the medical device remains in contact with blood for several hours during surgery. Accordingly, in the case where the medical material fixed to the medical device is eluted at high speed, it may be that the antithrombogenicity of the medical device decreases during the surgery, resulting in significant thrombus formation in the blood vessel circuit, thereby making the blood circuit unusable.

Thus, the upper limit of the content ratio of the repeating unit (A) based on all the structural units of the copolymer is specified to be 7 mol %. Accordingly, a medical material exhibiting excellent antithrombogenicity and also having moderately controlled water solubility may be obtained. As a result, a medical device that is excellent in terms of the above characteristics may be provided.

Therefore, according to the present disclosure, a medical material and a medical device, which particularly exhibit excellent antithrombogenicity even when used under conditions prone to thrombus formation, are provided.

Note that the above mechanism is based on theory, and the present disclosure is not limited to the above mechanism.

(Copolymer Contained in Medical Material)

The copolymer contained in the medical material according to the present disclosure is a copolymer comprising the repeating units (A) and (B), in which the content ratio of the repeating unit (A) based on all the structural units is within a specific range. Therefore, as long as the copolymer has the above composition, its terminus may not be particularly limited. The terminus are suitably determined according to the kind of raw material used, and are preferably hydrogen atoms. The structure of the copolymer may not be particularly limited, and may be any of a random copolymer, an alternating copolymer, a periodic copolymer, and a block copolymer.

It is preferable that the weight average molecular weight of the copolymer is 1,000 to 1,000,000. A weight average molecular weight within the above range is preferable in terms of solubility. In terms of the ease of covering with the coating layer, it is more preferable that the weight average molecular weight of the copolymer is 50,000 to 500,000. In the present disclosure, as used herein, "weight average molecular weight" means a value measured by gel permeation chromatography (GPC) using polystyrene as a reference material and tetrahydrofuran (THF) as a mobile phase.

Hereinafter, each structural unit (repeating unit) of the copolymer contained in the medical material will be described.

(I) Repeating Unit (A)

In the present disclosure, the copolymer contained in the medical material comprises a repeating unit (A) represented by the above formula (1).

In the above formula (1), $R^{11}$ is a hydrogen atom or a methyl group, and preferably a methyl group in terms of improving the antithrombogenicity.

In the above formula (1), Z is an oxygen atom or —NH—. Although an oxygen atom and —NH— are equal in terms of antithrombogenicity, in terms of durability, it is preferable that Z is —NH—. In the case where Z is —NH—, in the above formula (1), an amide structure is formed. This results in higher hydrolysis resistance than in the case where Z is an oxygen atom (i.e., the case where an ester structure is formed in the above formula (1)), which may be more suitable for applications in contact with a biological component over a long period of time.

In the above formula (1), $R^{12}$ is a $C_{1-6}$ linear or branched alkylene group. Specific examples thereof include, without limitation, a methylene group, an ethylene group, a trimethylene group, a propylene group, a tetramethylene group, a pentamethylene group, and a hexamethylene group. Among them, in terms of improving the antithrombogenicity, $C_{1-4}$ linear or branched alkylene groups are preferable, and a methylene group, an ethylene group, and a trimethylene group are more preferable, and an ethylene group and a trimethylene group are particularly preferable.

In the above formula (1), $R^{13}$ and $R^{14}$ are each independently a $C_{1-4}$ alkyl group. Specific examples thereof include, without limitation, linear or branched alkyl groups such as a methyl group, an ethyl group, a propyl group, an isopropyl group, a butyl group, an isobutyl group, a sec-butyl group, and a tert-butyl group. Among them, in terms of improving the antithrombogenicity, $C_{1-3}$ linear or branched alkyl groups are preferable, $C_{1-2}$ alkyl groups (methyl group, ethyl group) are more preferable, and a methyl group is particularly preferable.

In the above formula (1), $R^{15}$ is a $C_{1-6}$ linear or branched alkylene group. Specific examples thereof include, without limitation, the same groups as described above for $R^{12}$. Among them, in terms of improving the antithrombogenicity, $C_{1-4}$ linear or branched alkylene groups are preferable, and a methylene group, an ethylene group, and a trimethylene group are more preferable, and a trimethylene group is particularly preferable.

From above, in the above formula (1) representing the repeating unit (A), it is preferable that $R^{11}$ is a methyl group, Z is an oxygen atom or —NH—, $R^{12}$ is a $C_{1-4}$ alkylene group, $R^{13}$ and $R^{14}$ are each independently a $C_{1-2}$ alkyl group, and $R^{15}$ is a $C_{1-4}$ alkylene group. Further, in the above formula (1), it is particularly preferable that $R^{11}$ is a methyl group, $R^{12}$ is a $C_{2-3}$ alkylene group, Z is an oxygen atom or —NH—, $R^{13}$ and $R^{14}$ are each a $C_1$ alkyl group (methyl group), and $R^{15}$ is a $C_3$ alkylene group.

The copolymer contained in the medical material may be obtained by a polymerization reaction between a monomer that forms the repeating unit (A) described above (hereinafter also referred to as "monomer a") and a monomer that forms the repeating unit (B) described below in detail (hereinafter also referred to as "monomer b").

As the monomer a, for example, the following compounds where Z is an oxygen atom, or where Z is —NH—, are usable, without limitation. The following monomers may be used alone or as a mixture of two or more kinds. In addition, it is also possible to use a mixture of a compound where Z may be an oxygen atom and a compound where Z may be —NH—.

In the case where Z may be an oxygen atom, examples of monomers a include, without limitation, [2-(methacryloyloxy)ethyl]dimethyl-(3-sulfopropyl)ammonium hydroxide (compound of chemical formula (ii) in the Examples), [2-(acryloyloxy)ethyl]dimethyl-(3-sulfopropyl)ammonium hydroxide, {2-[(meth)acryloyloxy]ethyl}dimethyl-(2-sulfoethyl)ammonium hydroxide, {2-[(meth)acryloyloxy]ethyl}diethyl-(2-sulfoethyl)ammonium hydroxide, {2-[(meth)acryloyloxy]ethyl}diethyl-(3-sulfopropyl) ammonium hydroxide, {3-[(meth)acryloyloxy]propyl}dimethyl-(2-sulfoethyl)ammonium hydroxide, {3-[(meth)acryloyloxy]propyl}dimethyl-(3-sulfopropyl) ammonium hydroxide, {3-[(meth)acryloyloxy]propyl}diethyl-(2-sulfoethyl)ammonium hydroxide, and {3-[(meth)acryloyloxy]propyl}diethyl-(3-sulfopropyl) ammonium hydroxide. [2-(methacryloyloxy)ethyl] dimethyl-(3-sulfopropyl)ammonium hydroxide (sometimes abbreviated as "SBAC" herein) is preferable.

In addition, in the case where Z is —NH—, examples of monomers a include, without limitation, [3-(methacryloylamino)propyl]dimethyl(3-sulfopropyl)ammonium hydroxide (compound of chemical formula (i) in the examples), [3-(acryloylamino)propyl]dimethyl(3-sulfopropyl)ammonium hydroxide, {2-[(meth)acryloylamino]ethyl}dimethyl (2-sulfoethyl)ammonium hydroxide, {2-[(meth)acryloylamino]ethyl}dimethyl(3-sulfopropyl)ammonium hydroxide, {2-[(meth)acryloylamino]ethyl}diethyl(2-sulfoethyl)ammonium hydroxide, {2-[(meth)acryloylamino] ethyl}diethyl(3-sulfopropyl)ammonium hydroxide, {3-[(meth)acryloylamino]propyl}dimethyl(2-sulfoethyl) ammonium hydroxide, {3-[(meth)acryloylamino]propyl}diethyl(2-sulfoethyl)ammonium hydroxide, and {3-[(meth)acryloylamino]propyl}diethyl(3-sulfopropyl) ammonium hydroxide. [3-(methacryloylamino)propyl] dimethyl(3-sulfopropyl)ammonium hydroxide (sometimes abbreviated as "SBAA" herein) is preferable.

By using such a monomer having a betaine backbone, the coating layer of a medical device may be made antithrombogenic. Note that, as used herein, "(meth)acryl" means "acryl" and/or "methacryl", and "(meth)acryloyl" means "acryloyl" and/or "methacryloyl".

(II) Repeating Unit (B)

In the present disclosure, the copolymer contained in the medical material comprises a repeating unit (B) represented by the above formula (2).

In the above formula (2), $R^{21}$ is a hydrogen atom or a methyl group, and preferably a hydrogen atom in terms of improving the antithrombogenicity.

In the above formula (2), $R^{22}$ is a $C_{1-6}$ linear or branched alkylene group. Specific examples thereof include, without limitation, a methylene group, an ethylene group, a trimethylene group, a propylene group, a tetramethylene group, a pentamethylene group, and a hexamethylene group. Among them, in terms of improving the antithrombogenicity, $C_{1-3}$ linear or branched alkylene groups are preferable, and a methylene group and an ethylene group are more preferable, and an ethylene group is particularly preferable.

In the above formula (2), $R^{23}$ is a $C_{1-4}$ linear or branched alkyl group. Specific examples thereof include, without limitation, linear or branched alkyl groups such as a methyl group, an ethyl group, a propyl group, an isopropyl group, a butyl group, an isobutyl group, a sec-butyl group, and a tert-butyl group. Among them, in terms of improving the antithrombogenicity, $C_{1-3}$ linear or branched alkyl groups are preferable, $C_{1-2}$ alkyl groups (methyl group, ethyl group) are more preferable, and a methyl group is particularly preferable.

From above, in the above formula (2) representing the repeating unit (B), it is preferable that $R^{21}$ is a hydrogen atom or a methyl group, $R^{22}$ is a $C_{1-3}$ alkylene group, and $R^{23}$ is a $C_{1-2}$ alkyl group. Further, in the above formula (2), it is particularly preferable that $R^{21}$ is a hydrogen atom or a methyl group, $R^{22}$ is a $C_2$ alkylene group (ethylene group), and $R^{23}$ is a $C_1$ alkyl group (methyl group).

Examples of monomers b to form the repeating unit (B) include, without limitation, methoxymethyl acrylate, methoxyethyl acrylate (MEA), methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate. Preferred examples of monomers b include methoxymethyl acrylate, methoxyethyl acrylate (MEA), ethoxymethyl acrylate, ethoxyethyl acrylate, methoxymethyl methacrylate, methoxyethyl methacrylate, ethoxymethyl methacrylate, and ethoxyethyl methacrylate. In terms of availability, methoxyethyl acrylate (MEA) is more preferable. The above monomers may be used alone or as a mixture of two or more kinds.

(III) Content Ratio of Each Repeating Unit

In the present disclosure, the copolymer contains the repeating unit (A) in a proportion of 0.6 to 7 mol % based on all the structural units (100 mol %) of the copolymer. The repeating unit (A) is highly hydrophilic. Therefore, in the case where a large amount of repeating unit (A) is contained in the copolymer, such a copolymer exhibits excellent antithrombogenicity. Meanwhile, when the amount of repeating unit (A) is too large, the copolymer has increased water solubility. When such a medical material is applied to a medical device, the medical material may be released.

When the repeating unit (A) is present in a proportion of less than 0.6 mol % based on all the structural units of the copolymer, the antithrombogenicity-improving effect may not be sufficiently obtained, resulting in thrombus formation in severe environments, such as when used for a long period of time under conditions prone to thrombus formation. Meanwhile, when the repeating unit (A) is present in a proportion of more than 7 mol %, because of the action of the repeating unit (A) to impart water solubility, upon contact with a body fluid (e.g., blood), the medical material covering a medical device may be released from the substrate and eluted into the body fluid (contamination).

In terms of improving the antithrombogenicity and preventing the release of the medical material at the same time, the repeating unit (A) based on all the structural units is preferably 0.8 to 6 mol %, more preferably 0.9 to 4.7 mol %, and particularly preferably 1 to 4 mol %.

In the copolymer contained in the medical material, as long as the repeating unit (A) based on all the structural units is within the above range, the content ratio of the repeating unit (B) is not particularly limited. However, it is preferable that the repeating unit (B) is contained, for example, in a proportion of 60 mol % or more based on all the structural units of the copolymer, more preferably in a proportion of 80 mol % or more, and particularly preferably in a proportion of 90 mol % or more. Meanwhile, in relation to the repeating unit (A), the upper limit thereof is 99.4 mol %.

The copolymer contained in the medical material may contain other structural units aside from the repeating units (A) and (B), but is preferably composed only of the repeating units (A) and (B). That is, in the copolymer contained in the medical material, it is preferable in the total amount of the repeating unit (A) and the repeating unit (B) is 100 mol %.

Thus, it is preferable that the copolymer includes 0.6 to 7 mol % the repeating unit (A) and 99.4 to 93 mol % the repeating unit (B) (the total amount of the repeating unit (A) and the repeating unit (B) is 100 mol %). When the copolymer has the above composition, such a copolymer exhibits high antithrombogenicity even under severe conditions prone to thrombus formation. At the same time, the medical material covering a medical device may be prevented from being released from the substrate and eluted into a body fluid (contamination).

Further, it is more preferable that the copolymer contained in the medical material includes 0.8 to 6 mol % the repeating unit (A) and 99.2 to 94 mol % the repeating unit (B) (the total amount of the repeating unit (A) and the repeating unit (B) is 100 mol %). Further, it is still more preferable that the copolymer includes 0.9 to 4.7 mol % the repeating unit (A) and 99.1 to 95.3 mol % the repeating unit (B) (the total amount of the repeating unit (A) and the repeating unit (B) is 100 mol %). Further, it is particularly preferable that the copolymer includes 1 to 4 mol % the repeating unit (A) and 99 to 96 mol % the repeating unit (B) (the total amount of the repeating unit (A) and the repeating unit (B) is 100 mol %).

In the present disclosure, as the proportions of the repeating unit (A), the repeating unit (B), and repeating units derived from other monomers in the copolymer, values determined by NMR spectroscopy should be employed. For example, in the case of a copolymer composed of the repeating unit (A) and the repeating unit (B), $^1$H-NMR integration values of the alkylene group (i.e., $R^{15}$) and alkoxy group (i.e., $-OR^{23}$) on the nitrogen atom, which are characteristic structures of the repeating units (A) and (B), respectively, are determined, and, based on the ratio between the integration values, the proportions of the repeating unit (A) and the repeating unit (B) in the copolymer can be analyzed. In addition, in the case where the peaks overlap in the $^1$H-NMR measurement, $^{13}$C-NMR may be used for calculation.

(IV) Other Structural Units

As described above, the copolymer contained in the medical material may preferably be composed only of the repeating units (A) and (B), but may also contain other repeating units. That is, in another embodiment of the invention, the copolymer contained in the medical material may contain structural units (repeating units) derived from the monomer a, the monomer b, and other monomers copolymerizable therewith (hereinafter also simply referred to as "other monomers").

Examples of other monomers copolymerizable with the monomer a and the monomer b include, without limitation, acrylamide, N,N-dimethylacrylamide, N,N-diethylacrylamide, aminomethyl acrylate, aminoethyl acrylate, aminoisopropyl acrylate, diaminomethyl acrylate, diaminoethyl acrylate, diaminobutyl acrylate, methacrylamide, N,N-dimethylmethacrylamide, N,N-diethylmethacrylamide, aminomethyl methacrylate, aminoethyl methacrylate, diaminomethyl methacrylate, diaminoethyl methacrylate, methyl acrylate, ethyl acrylate, isopropyl acrylate, butyl acrylate, 2-ethylhexyl acrylate, methyl methacrylate, ethyl methacrylate, butyl methacrylate, hexyl acrylate, hexyl methacrylate, ethylene, propylene, N-vinylacetamide, N-isopropenylacetamide, and N-(meth)acryloylmorpholine.

The proportion of repeating units derived from the above other monomers based on all the structural units of the copolymer is not particularly limited, and is, for example, more than 0 mol % and less than 39 mol %, preferably more than 0 mol % and less than 33 mol %, more preferably more than 0 mol % and less than 9 mol %, and particularly preferably more than 0 mol % and less than 3 mol %.

(Method for Producing Copolymer)

The proportions of the repeating unit (A), the repeating unit (B), and repeating units derived from other monomers in the copolymer may be arbitrarily adjusted by changing the proportions of monomers used for polymerization. More specifically, at the time of polymerization, it may be necessary that the monomer a for forming the repeating unit (A) is added in a proportion of 0.6 to 7 mol % based on the total number of moles of all the monomers used. Further, at this time, it is preferable that the monomer b for forming the repeating unit (B) is added in a proportion of 99.4 to 93 mol % based on the total number of moles of all the monomers used. Basically, with respect to a copolymer obtained by the copolymerization of the monomer a, the monomer b, and optionally added other monomers, in the case where molecular weight fractionation or the like is not performed, the feeding ratios of the monomers used for copolymerization are equivalent to the content ratios of the corresponding repeating units in the obtained copolymer.

The method for producing the copolymer contained in the medical material according to the present disclosure is not particularly limited. For example, known polymerization methods, such as radical polymerization, anionic polymerization, and cationic polymerization, may be employed, and it is preferable to use radical polymerization. As a method for producing the copolymer contained in the medical material according to the present disclosure, it is also possible to employ plasma polymerization by radiation or UV light, for example, thereby forming a coating layer containing the copolymer on the substrate surface.

As a method for polymerizing the monomers, a method in which at least one kind of monomer a corresponding to the repeating unit (A) (e.g., [2-(methacryloyloxy)ethyl]dimethyl-(3-sulfopropyl)ammonium hydroxide] (SBAC) or [3-(methacryloylamino)propyl]dimethyl(3-sulfopropyl)ammonium hydroxide (SBAA)], at least one kind of monomer b corresponding to the repeating unit (B) (e.g., methoxyethyl acrylate (MEA)), and other monomers as necessary may be stirred and heated in a polymerization solvent together with a polymerization initiator, thereby causing copolymerization, may be used.

In terms of controlling the molecular weight, it is preferable that the polymerization temperature is 30° C. to 100° C. The polymerization reaction is usually carried out for 30 minutes to 24 hours.

Preferred examples of polymerization solvents may include, without limitation, aqueous solvents including water; alcohols such as methanol, ethanol, propanol, and n-butanol; polyalcohols such as ethylene glycol, diethylene glycol, propylene glycol, and dipropylene glycol; and the like. Methanol, ethanol, and propanol are particularly preferable. They may be used alone, and it is also possible to use two or more kinds together.

The monomer concentration (solids concentration) in the polymerization solvent may be 10 to 90 wt %, preferably 15 to 80 wt %, based on the entire reaction solution. Note that the monomer concentration relative to the polymerization solvent refers to the concentration of the total weight of the monomer a, the monomer b, and optionally contained other monomers copolymerizable therewith (hereinafter "the monomer a, the monomer b, and optionally contained other monomers copolymerizable therewith" is also referred to as "polymerization monomers").

The polymerization solvent having added thereto the polymerization monomers may be subjected to a degassing treatment before the addition of a polymerization initiator. The degassing treatment may be such that, for example, the polymerization solvent having added thereto the polymerization monomers is bubbled with an inert gas, such as nitrogen gas or argon gas, for about 0.5 to 5 hours. At the time of the degassing treatment, the polymerization solvent having added thereto the polymerization monomers may be heated to about 30°C to 100° C.

For the production of the copolymer, known polymerization initiators may be used without limitation. For example, azo polymerization initiators such as 2,2'-azobisisobutyronitrile, 2,2'-azobis(4-methoxy-2,4-dimethylvaleronitrile), and 2,2'-azobis(2,4-dimethylvaleronitrile); and redox polymerization initiators obtained by combining an oxidizing agent, such as a persulfate such as potassium peroxodisulfate (KPS), sodium persulfate, and ammonium persulfate, or a peroxide such as hydrogen peroxide, t-butyl peroxide, and methyl ethyl ketone peroxide, with a reducing agent, such as sodium sulfite, sodium hydrogensulfite, or ascorbic acid, may be used.

The amount of polymerization initiator incorporated may be, for example, 0.0001 to 1 mol per mole of all the monomers used for copolymer production.

Further, chain transfer agents, polymerization rate regulators, surfactants, and other additives may also be suitably used for polymerization.

The atmosphere in which the polymerization reaction may be carried out is not limited, and the reaction may be carried out in ambient atmosphere, an inert gas atmosphere such as nitrogen gas or argon gas, or the like. In addition, the reaction mixture may be stirred during the polymerization reaction.

The copolymer after polymerization may be purified by a general purification method, such as reprecipitation, dialysis, ultrafiltration, or extraction.

The copolymer after purification may be dried by any method, such as by freeze drying, vacuum drying, spray drying, or drying by heating. However, in terms of not significantly affecting the physical properties of the polymer, freeze drying or vacuum drying are preferred.

(Other Components)

The medical material according to the present disclosure may contain other components aside from the copolymer. Examples of other components include, without limitation, unreacted monomers that have not reacted during polymerization, as well as various additives such as crosslinking agents, thickeners, preservatives, and pH adjusters.

It is preferable that the content of unreacted polymerization monomers in the obtained copolymer is 0.01 wt % or less based on the entire copolymer. The lower the content of unreacted polymerization monomers, the better. Thus, the lower limit may be, for example, 0 wt %. The content of residual monomers may be measured by a method known to those skilled in the art, such as high-speed liquid chromatography.

The medical material of the present disclosure may be used in the form of the obtained copolymer, and may also be processed into a gel, a solution, or the like before use. For example, the medical material may be used in the form of a coating agent prepared by dissolving the copolymer in a solvent.

In the case of a coating agent, the solvent to be used is not limited as long as it may be capable of dissolving the copolymer. Examples thereof include, without limitation, alcohol solvents such as methanol, ethanol, isopropanol, and butanol; water; and non-proton-donating organic solvents such as chloroform, tetrahydrofuran, acetone, dioxane, and benzene. The above solvents may be used alone or as a mixture of two or more kinds. As a mixed solvent, a water-alcohol solvent is preferable, and a water-methanol mixed solvent is particularly preferable.

The amount of copolymer contained in the coating agent may be arbitrarily set, and it is also possible to use a solution prepared by dissolving the copolymer to saturation. For example, the amount is preferably 0.01 to 50 wt %, more preferably 0.1 to 50 wt %, based on the entire coating agent.

The coating agent may be composed of the copolymer and the solvent, and may also optionally contain other components such as crosslinking agents, thickeners, preservatives, and pH adjusters. When a crosslinking agent is included, the copolymer may be more firmly fixed to the substrate surface. In particular, the repeating unit (A) included in the medical material is highly reactive with a crosslinking agent, and thus the medical material may be more firmly fixed to the substrate surface.

[Medical Device]

Next, a medical device according to embodiments of the present disclosure will be described in detail. According embodiments, provided is a medical device including a substrate and, on the substrate surface, a coating layer containing the above medical material.

As described above, the medical material of the present disclosure has excellent antithrombogenicity. Therefore, by using the above medical material, a medical device having excellent antithrombogenicity may be provided.

(Substrate)

In the medical device of the present disclosure, the substrate surface may be covered with the above medical material. Materials for the substrate are not limited, and examples thereof include, without limitation, various polymer materials including polyolefins, such as polyethylene, polypropylene, and ethylene-α-olefin copolymers, and modified polyolefins; polyamides; polyimides; polyurethanes; polyesters such as polyethylene terephthalate (PET), polybutylene terephthalate (PBT), polycyclohexane terephthalate, and polyethylene-2,6-naphthalate; polyvinyl chlorides; polyvinylidene chlorides (PVDC); polycarbonates; fluororesins such as polytetrafluoroethylene (PTFE) and ethylene-tetrafluoroethylene copolymers (ETFE); and the like, as well as metals such as SUS, ceramic, carbon, and composite materials thereof.

The shape of the substrate may be suitably selected according to the intended use of the medical device or the like, and the substrate may be in the shape of, for example, a tube, a sheet, a rod, or the like. The form of the substrate is not limited to a molded body using the above material alone, and the substrate may also be used in the form of a blended molded article, an alloyed molded article, a multi-layered molded article, or the like. The substrate may have a monolayer or laminated structure. In the case of a laminated substrate, the substrates of the layers may be the same or different from each other. However, in the case where it is desired to swell the substrate with a solvent to firmly fix the copolymer, at least as a material present on the substrate surface, a material that may be swollen well with the solvent of the coating agent of the medical material is preferable.

In the present disclosure, "substrate surface" may be a side of the substrate that faces a biological tissue or a body fluid such as blood. When a coating layer made of the copolymer-containing medical material is formed on the substrate surface, the antithrombogenicity of the substrate surface may be improved. In the medical device according to the present disclosure, it may be necessary that the copolymer-containing coating layer is formed on a side of the substrate that faces a biological tissue or a body fluid such as blood, but this should not interfere with the formation of the coating layer also on other sides.

In order to enhance the stability of the coating layer on the substrate surface, the substrate may be surface-treated before forming the coating layer on the substrate surface. Examples of methods for surface-treating the substrate include, without limitation, a method that applies active energy rays (electron beam, UV, X-ray, etc.), a method that utilizes plasma discharge (arc discharge, corona discharge, or glow discharge), a method that applies a high electric field, a method that allows ultrasonic vibration through a polar liquid (water, etc.) to act, and a method of treating the surface with ozone gas.

(Method for Forming Coating Layer)

In the medical device according to the present disclosure, the substrate surface may be covered with the medical material to form a coating layer.

The formation of a coating layer on the substrate surface may be performed by applying a coating liquid containing the medical material (e.g., the above coating agent), thereby covering the substrate surface, or by applying a polymerization solvent containing polymerization monomers for obtaining a copolymer to the substrate surface, followed by plasma polymerization. In terms of the ease of production, it may be preferable that the coating layer is formed by covering the substrate surface with a coating liquid containing the medical material. Note that "covering" includes not only the mode in which the entire surface of the substrate is completely covered with the coating layer, but also the mode in which the surface of the substrate is partially covered with the coating layer, that is, the mode in which the coating layer is attached to a part of the substrate surface.

In the case where the coating layer is formed by covering the substrate surface with a coating liquid containing the medical material, for the method for preparing a coating liquid containing the medical material, the method for preparing a coating agent described above may be suitably taken into consideration.

As the method for applying a coating liquid containing the medical material to the substrate surface, known methods may be employed without limitation. Examples thereof include, without limitation, dip coating, spraying, spin coating, dripping, doctor blading, brush coating, roll coating, air knife coating, curtain coating, wire bar coating, and gravure coating.

The thickness of the coating liquid (coating layer) may be suitably adjusted according to the intended use of the medical device and is not particularly limited. For example, the layer is formed to a thickness of 0.1 µm or less.

By drying the substrate surface having applied thereto the copolymer-containing coating liquid, a coating layer may be formed on the substrate surface. The drying step may be suitably set considering the glass transition temperature of the substrate or the like, and is, for example, 15 to 50° C. The atmosphere during the drying step is not limited, and the step may be performed in ambient atmosphere or an inert gas atmosphere such as nitrogen gas or argon gas.

(Examples of Medical Devices)

Examples of medical devices according to the present disclosure include, without limitation, implantable prostheses and treating instruments, artificial organs for extracorporeal circulation, catheters, and guidewires. Specific examples thereof include, without limitation, artificial blood vessels, artificial tracheas, and stents inserted into, or to replace, blood vessels or lumens; implantable medical instruments such as artificial skins and artificial pericardia; artificial organ systems such as artificial heart systems, artificial lung systems, artificial heart-lung systems, artificial kidney systems, artificial liver systems, and immunoregulation systems; catheters inserted into or indwelled in blood vessels, such as indwelling needles, IVH catheters, catheters for liquid medicine administration, thermodilution catheters, angiographic catheters, vasodilatation catheters, dilators, and introducers, as well as guidewires, stylets, and the like for these catheters; various suction catheters such as stomach tube catheters, nutrition catheters, feeding (ED) tubes, urethral catheters, urine drainage catheters, balloon catheters, and tracheal suction catheters; and catheters inserted into or indwelled in biological tissues other than blood vessels, such as drainage catheters. In particular, an artificial lung system, for example, may be used continuously for a long period of time and also has several steps at tube connections and the like. Accordingly, the present disclosure may be suitable for use as an artificial lung system or an artificial heart-lung system, which contacts a large amount of blood.

EXAMPLES

The advantageous effects of the present disclosure will be described hereinafter through examples and comparative examples. However, the technical scope of the present disclosure is not limited only to the following examples.

Example 1

Copolymer of SBAA (in Formula (1), Z=—NH—) and MEA (Repeating Unit (A): 4.7 mol %)

5 g (38.4 mmol) of methoxyethyl acrylate (MEA) and 0.55 g (1.9 mmol) of [3-(methacryloylamino)propyl]dimethyl(3-sulfopropyl)ammonium hydroxide (SBAA, compound of the following chemical formula (i)) were dissolved in 22 g of methanol, placed in a four-necked flask, and bubbled with $N_2$ at 50° C. for 1 hour.

[Chemical Formula 5]

[Chemical Formula (5)]

Subsequently, a solution prepared by dissolving 0.006 g of 2,2'-azobis(4-methoxy-2,4-dimethylvaleronitrile) (V-70, manufactured by Wako Pure Chemical Industries) in 1 mL of methanol was added to the methanol solution having dissolved therein the polymerization monomers, followed by polymerization at 50° C. for 5 hours. The polymerization liquid was added dropwise to diethyl ether, and the precipitated copolymer was recovered to give a polymer (1). The content ratio of the repeating unit (A) in the polymer (1) was measured by $^1$H-NMR. As a result, the ratio was the same as the value calculated from the above feeding amount. In addition, the content ratio of the repeating unit (B) was also the same as the value calculated from the feeding amount (95.3 mol %).

Example 2

Copolymer of SBAA (in Formula (1), Z=—NH—) and MEA (Repeating Unit (A): 3.2 mol %)

A polymer (2) was obtained in the same manner as in Example 1, except that the amounts of SBAA and methanol used in the preparation of the copolymer in Example 1 were changed to 0.37 g (1.3 mmol) and 21 g, respectively. The content ratio of the repeating unit (A) in the polymer (2) was measured by $^1$H-NMR. As a result, the ratio was the same as the value calculated from the above feeding amount. In addition, the content ratio of the repeating unit (B) was also the same as the value calculated from the feeding amount (96.8 mol %).

Example 3

Copolymer of SBAA (in Formula (1), Z=—NH—) and MEA (Repeating Unit (A): 0.9 mol %)

A polymer (3) was obtained in the same manner as in Example 1, except that the amounts of SBAA and methanol used in the preparation of the copolymer in Example 1 were changed to 0.1 g (0.3 mmol) and 20 g, respectively. The content ratio of the repeating unit (A) in the polymer (3) was measured by $^1$H-NMR. As a result, the ratio was the same as the value calculated from the above feeding amount. In addition, the content ratio of the repeating unit (B) was also the same as the value calculated from the feeding amount (99.1 mol %).

Example 4

Copolymer of SBAC (in Formula (1), Z=Oxygen Atom) and MEA (Repeating Unit (A): 3.3 mol %)

A polymer (4) was obtained in the same manner as in Example 1, except that SBAA used in the preparation of the copolymer in Example 1 was changed to [2-(methacryloyloxy)ethyl]dimethyl-(3-sulfopropyl)ammonium hydroxide (SBAC, compound of the following chemical formula (ii)], further the amount thereof was changed to 0.37 g (1.3 mmol), and the amount of methanol used was changed to 20 g. The content ratio of the repeating unit (A) in the polymer (4) was measured by $^1$H-NMR. As a result, the ratio was the same as the value calculated from the above feeding amount. In addition, the content ratio of the repeating unit (B) was also the same as the value calculated from the feeding amount (96.7 mol %).

[Chemical Formula 6]

[Chemical Formula (6)]

Example 5

Copolymer of SBAC (in Formula (1), Z=Oxygen Atom) and MEA (Repeating Unit (A): 1.7 mol %)

A polymer (5) was obtained in the same manner as in Example 4, except that the amounts of SBAC and methanol used in the preparation of the copolymer in Example 4 were changed to 0.18 g (0.6 mmol) and 20 g, respectively. The content ratio of the repeating unit (A) in the polymer (5) was measured by $^1$H-NMR. As a result, the ratio was the same as the value calculated from the above feeding amount. In addition, the content ratio of the repeating unit (B) was also the same as the value calculated from the feeding amount (98.3 mol %).

Example 6

Copolymer of SBAC (in Formula (1), Z=Oxygen Atom) and MEA (Repeating Unit (A): 0.7 mol %)

A polymer (6) was obtained in the same manner as in Example 4, except that the amounts of SBAC and methanol used in the preparation of the copolymer in Example 4 were changed to 0.07 g (0.3 mmol) and 20 g, respectively. The content ratio of the repeating unit (A) in the polymer (6) was measured by $^1$H-NMR. As a result, the ratio was the same as the value calculated from the above feeding amount. In addition, the content ratio of the repeating unit (B) was also the same as the value calculated from the feeding amount (99.3 mol %).

Comparative Example 1

Copolymer of SBAA (in Formula (1), Z=—NH—) and MEA (Repeating Unit (A): 21.1 mol %)

A comparative polymer (1) was obtained in the same manner as in Example 1, except that the amounts of SBAA and methanol used in the preparation of the copolymer in Example 1 were changed to 3.0 g (10.3 mmol) and 32 g, respectively. The content ratio of the repeating unit (A) in the comparative polymer (1) was measured by $^1$H-NMR. As a result, the ratio was the same as the value calculated from the above feeding amount. In addition, the content ratio of the repeating unit (B) was also the same as the value calculated from the feeding amount (78.9 mol %).

Comparative Example 2

Copolymer of SBAA (in Formula (1), Z=—NH—) and MEA (Repeating Unit (A): 8.9 mol %)

A comparative polymer (2) was obtained in the same manner as in Example 1, except that the amounts of SBAA and methanol used in the preparation of the copolymer in Example 1 were changed to 1.1 g (3.8 mmol) and 24 g, respectively. The content ratio of the repeating unit (A) in the comparative polymer (2) was measured by $^1$H-NMR. As a result, the ratio was the same as the value calculated from the above feeding amount. In addition, the content ratio of the repeating unit (B) was also the same as the value calculated from the feeding amount (91.1 mol %).

Comparative Example 3

Copolymer of SBAA (in Formula (1), Z=—NH—) and MEA (Repeating Unit (A): 0.4 mol %)

A comparative polymer (3) was obtained in the same manner as in Example 1, except that the amounts of SBAA and methanol used in the preparation of the copolymer in Example 1 were changed to 0.05 g (0.2 mmol) and 20 g, respectively. The content ratio of the repeating unit (A) in the comparative polymer (3) was measured by $^1$H-NMR. As a result, the ratio was the same as the value calculated from the above feeding amount. In addition, the content ratio of the repeating unit (B) was also the same as the value calculated from the feeding amount (99.6 mol %).

Comparative Example 4

Copolymer of SBAC (in Formula (1), Z=Oxygen Atom) and MEA (Repeating Unit (A): 10.1 mol %)

A comparative polymer (4) was obtained in the same manner as in Example 4, except that the amounts of SBAC and methanol used in the preparation of the copolymer in Example 4 were changed to 1.2 g (4.3 mmol) and 20 g, respectively. The content ratio of the repeating unit (A) in the comparative polymer (4) was measured by $^1$H-NMR. As a result, the ratio was the same as the value calculated from the above feeding amount. In addition, the content ratio of the repeating unit (B) was also the same as the value calculated from the feeding amount (89.9 mol %).

Comparative Example 5

Copolymer of SBAC (in Formula (1), Z=Oxygen Atom) and MEA (Repeating Unit (A): 0.4 mol %)

A comparative polymer (5) was obtained in the same manner as in Example 4, except that the amounts of SBAC and methanol used in the preparation of the copolymer in Example 4 were changed to 0.04 g (0.1 mmol) and 20 g, respectively. The content ratio of the repeating unit (A) in the comparative polymer (5) was measured by $^1$H-NMR. As a result, the ratio was the same as the value calculated from the above feeding amount. In addition, the content ratio of the repeating unit (B) was also the same as the value calculated from the feeding amount (99.6 mol %).

Comparative Example 6

Copolymer of CBA and MEA (CBA-Derived Structural Unit: 0.84 mol %)

A comparative polymer (6) was obtained in the same manner as in Example 1, except that SBAA in the preparation of the copolymer in Example 1 was replaced with 0.07 g (0.33 mmol) of N-methacryloyloxyethyl-N,N-dimethyl-ammonium-α-N-methylcarboxybetaine (CBA, compound of the following chemical formula (iii)), and the amount of methanol used was changed to 25.5 g. The content ratio of the CBA-derived structural unit in the comparative polymer (6) was measured by $^1$H-NMR. As a result, the ratio was the same as the value calculated from the above feeding amount. In addition, the content ratio of the repeating unit (B) was also the same as the value calculated from the feeding amount (99.16 mol %).

[Chemical Formula 7]

[Chemical Formula 7]

Comparative Example 7

(Homo)Polymer of MEA (Repeating Unit (A): 0 mol %)

A comparative polymer (7) was obtained in the same manner as in Example 1, except that 5 g (38.4 mmol) of MEA in the preparation of the copolymer in Example 1 was used alone. That is, the comparative polymer (7) was obtained as a homopolymer of MEA. In addition, the weight average molecular weight of the comparative polymer (7) was 130,000. Note that the weight average molecular weight was measured by GPC as described above.

The polymers (1) to (6) and comparative polymers (1) to (7) obtained in the examples and comparative examples were purified by reprecipitation in diethyl ether. Subsequently, these copolymers and polymers were dried by vacuum drying and subjected to the following tests.

Test Example 1

Polymer (Copolymer or Polymer) Solubility Test 0.1-g samples were weighed from the polymers (1) to (6) and comparative polymers (1) to (2) and (4) obtained in the examples and comparative examples, and placed in separate test tubes made of glass.

5 g of physiological saline was added to each test tube and stirred, and the solubility of the polymer was examined. As visually observed, in the case where the polymer maintained its form as placed in the glass test tube, such a polymer was considered as insoluble in water. In the case where there was no insoluble matter, or it was slightly cloudy but dispersed, such a polymer was considered to be dissolved in water.

TABLE 1

| Composition of Medical Material | Z in Formula (1) | Solubility in Water |
|---|---|---|
| Example 1 (MEA-SBAA copolymer, SBAA: 4.7 mol %) | —NH— | Insoluble |
| Example 2 (MEA-SBAA copolymer, SBAA: 3.2 mol %) | —NH— | Insoluble |
| Example 3 (MEA-SBAA copolymer, SBAA: 0.9 mol %) | —NH— | Insoluble |
| Example 4 (MEA-SBAC copolymer, SBAC: 3.3 mol %) | —O— (oxygen atom) | Insoluble |
| Example 5 (MEA-SBAC copolymer, SBAC: 1.7 mol %) | —O— (oxygen atom) | Insoluble |
| Example 6 (MEA-SBAC copolymer, SBAC: 0.7 mol %) | —O— (oxygen atom) | Insoluble |
| Comparative Example 1 (MEA-SBAA copolymer, SBAA: 21.1 mol %) | —NH— | Dissolved |
| Comparative Example 2 (MEA-SBAA copolymer, SBAA: 8.9 mol %) | —NH— | Dissolved |
| Comparative Example 4 (MEA-SBAC copolymer, SBAC: 10.1 mol %) | —O— (oxygen atom) | Dissolved |

As shown in Table 1, even in the case of a copolymer containing the repeating unit (A) having high hydrophilicity, when the repeating unit (A) is 7 mol % or less based on all the structural units of the copolymer, such a copolymer is not dissolved in physiological saline.

This result shows that when the repeating unit (A) is 7 mol % or less based on all the structural units of the copolymer, the substrate can be suitably coated with the medical material, and also the medical material (coating layer) can be more effectively prevented from being released from the substrate and contaminating blood.

In addition, when the repeating unit (A) is 4.7 mol % or less based on all the structural units of the copolymer, the dissolution in physiological saline can be particularly inhibited. Therefore, it is suggested that when the repeating unit (A) is 4.7 mol % or less based on all the structural units of the copolymer, the medical material (coating layer) can be even more effectively prevented from being released from the substrate and contaminating blood.

Test Example 2

Antithrombogenicity Test (Preparation of Coating Agent)

0.5 wt % methanol solutions of the above polymers (1) to (6) and comparative polymers (3) and (5) to (7) obtained in the examples and comparative examples were prepared and used as coating agents.

(Production of Medical Device)

At each end of a soft vinyl chloride tube 30 cm in overall length×8 mm in inner diameter (tube 1), 1 cm of an end of a soft vinyl chloride tube 5 cm in overall length×6 mm in inner diameter×9 mm in outer diameter (tube 2) was inserted, thereby producing a stepped tube.

Figure 1:
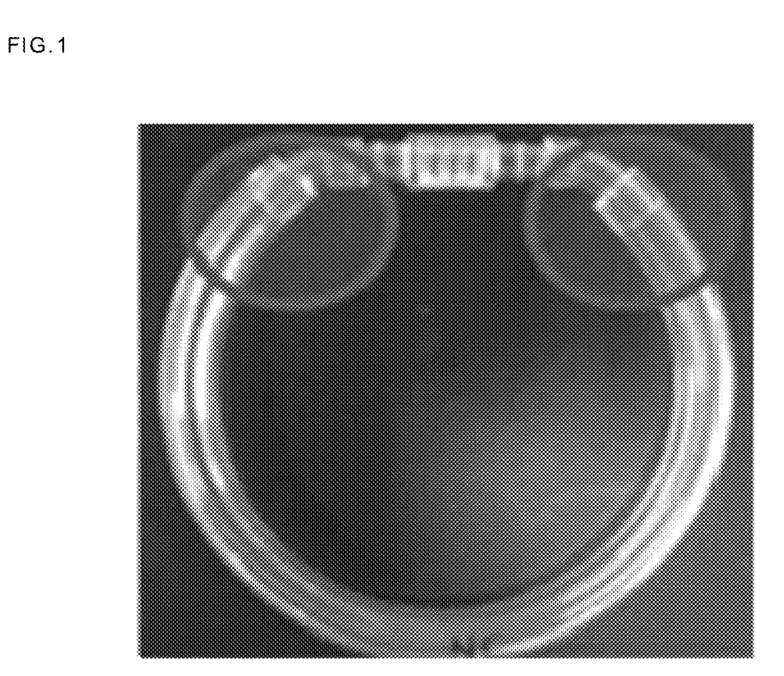
FIG. 1 shows a tube (stepped tube) used in the Examples, with both ends being connected by a connector.

FIG. 1 shows the produced stepped tube. In FIG. 1, the circled portions each show the joint between the tubes 1 and 2.

Figure 2:
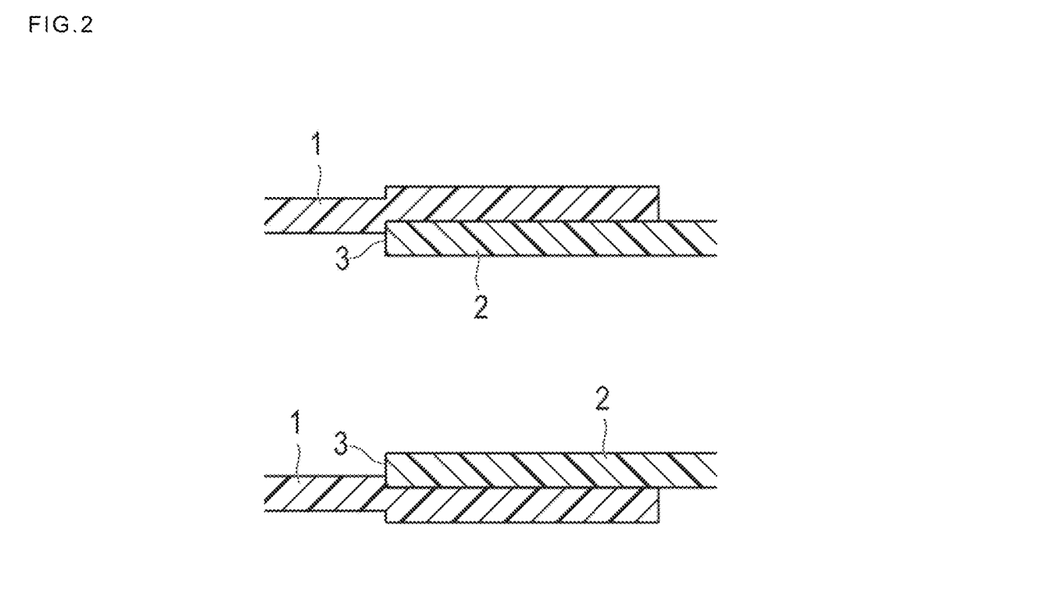
FIG. 2 is an enlarged view schematically showing a longitudinal cross-section of the joint between tubes 1 and 2 in FIG. 1.

FIG. 2 is an enlarged view schematically showing the joint between the tubes 1 and 2 in FIG. 1. The inner diameter of the tube 2 is smaller than the inside diameter of the tube 1, and thus a stepped surface 3 is formed. In the case where blood is passed through the stepped tube, it is highly likely that thrombus formation occurs at the stepped surface 3.

Using the produced stepped tube as a substrate, the above coating agent was passed through the stepped tube to apply the coating agent to the substrate surface. Subsequently, the stepped tube was dried at room temperature (25° C.), thereby forming a coating layer containing a medical material on the substrate surface (the lumenal surface of the stepped tube). At this time, the (co)polymers obtained in the above examples and comparative examples were each dissolved in methanol to prepare a 0.5 wt % solution, and used for dip coating to form the coating layer.

(Antithrombogenicity Test)

In order to evaluate the antithrombogenicity of a medical material under severe conditions prone to thrombus formation, the following test system was established using the above stepped tube having formed therein a coating layer.

That is, the lumen of the stepped tube having formed therein a coating layer was filled with 6 ml of a liquid prepared by diluting human fresh blood 2-fold with physiological saline (diluted blood). Both ends of the stepped tube were connected with a connector, fixed to a cylindrical rotator, and rotated at 40 rpm for 2 hours. Subsequently, the circulating blood was removed from the stepped tube, and thrombus attachment (indicated by the reference numeral "4" in FIG. 4) to the joint between the tubes 1 and 2 (stepped surface) was visually observed. Here, "fresh blood" means blood collected from a healthy donor by whole blood transfusion within 30 minutes ago. Note that the fresh blood has no anticoagulant added.

Figure 3:
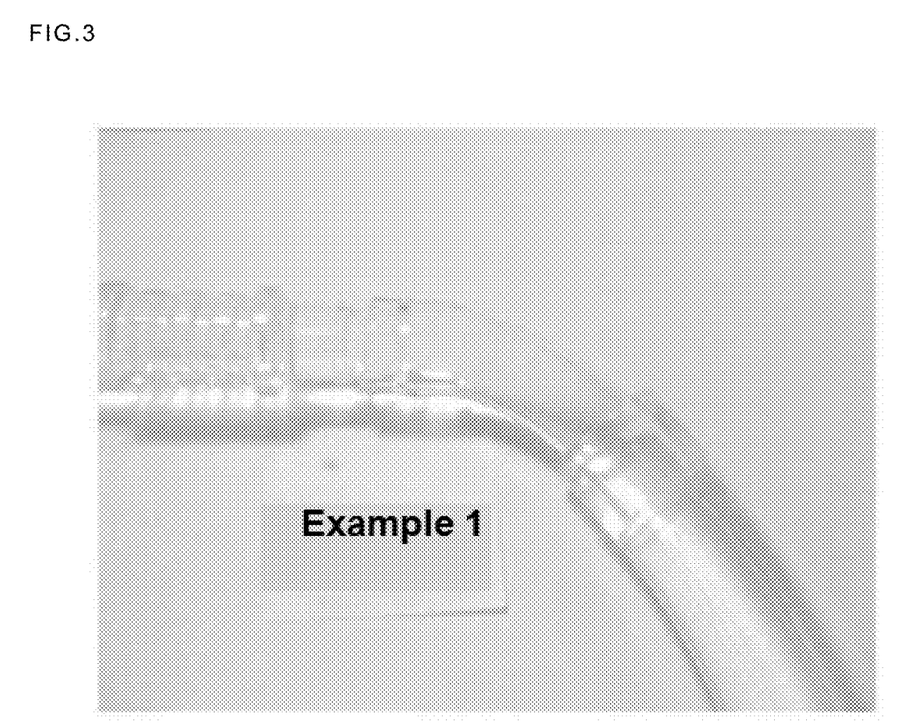
FIG. 3 is an enlarged photograph of a joint in a stepped tube having applied thereto a medical material containing the copolymer produced in Example 1, immediately after the antithrombogenicity test.
Figure 4:
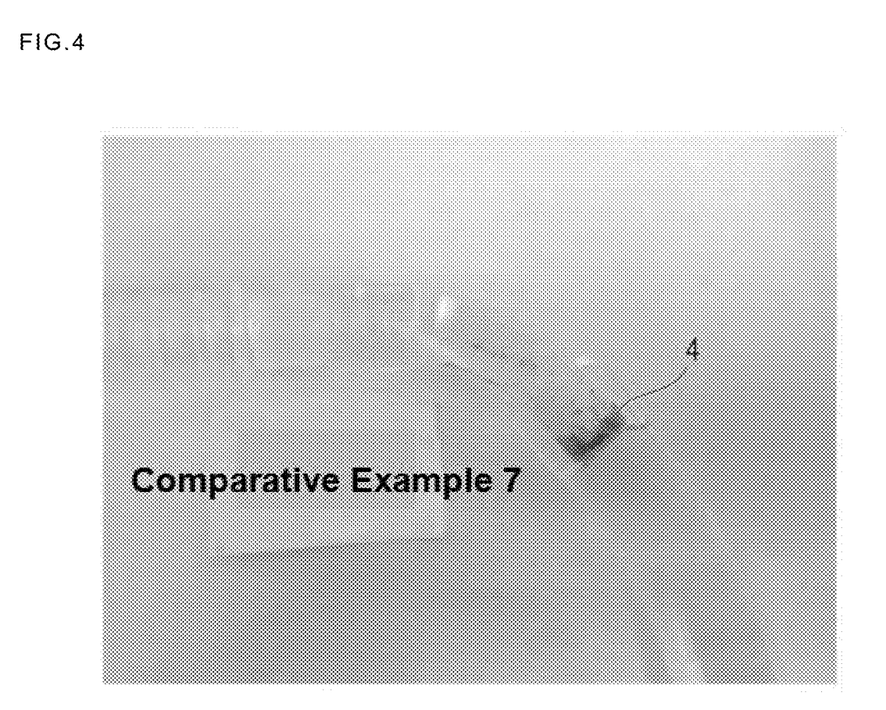
FIG. 4 is an enlarged photograph of a joint in a stepped tube having applied thereto a medical material containing the copolymer produced in Comparative Example 7, immediately after the antithrombogenicity test.

FIG. 3 and FIG. 4 are enlarged photographs of joints in stepped tubes having applied thereto coating layers each containing the copolymer produced in Example 1 or the polymer produced in Comparative Example 7, immediately after the antithrombogenicity test. In the stepped tube having applied thereto the copolymer according to the present disclosure, thrombus formation was not observed (FIG. 3). Meanwhile, in the stepped tube having applied thereto the polymer of Comparative Example 7, a thrombus 4 was observed at the joint (FIG. 4).

TABLE 2

| Composition of Medical Material | Z in Formula (1) | Thrombus Formation at Steps |
|---|---|---|
| Example 1 (MEA-SBAA copolymer, SBAA: 4.7 mol %) | —NH— | Not formed |
| Example 2 (MEA-SBAA copolymer, SBAA: 3.2 mol %) | —NH— | Not formed |
| Example 3 (MEA-SBAA copolymer, SBAA: 0.9 mol %) | —NH— | Not formed |
| Example 4 (MEA-SBAC copolymer, SBAC: 3.3 mol %) | —O— (oxygen atom) | Not formed |
| Example 5 (MEA-SBAC copolymer, SBAC: 1.7 mol %) | —O— (oxygen atom) | Not formed |
| Example 6 (MEA-SBAC copolymer, SBAC: 0.7 mol %) | —O— (oxygen atom) | Not formed |

TABLE 2-continued

| Composition of Medical Material | Z in Formula (1) | Thrombus Formation at Steps |
|---|---|---|
| Comparative Example 3 (MEA-SBAA copolymer, SBAA: 0.4 mol %) | —NH— | Formed |
| Comparative Example 5 (MEA-SBAC copolymer, SBAC: 0.4 mol %) | —O— (oxygen atom) | Formed |
| Comparative Example 6 (MEA-CBA copolymer, CBA: 0.84 mol %) | — (CBA) | Formed |
| Comparative Example 7 (MEA polymer, SBAA: 0 mol %, SBAC: 0 mol %) | — (no SBAA, no SBAC) | Formed |

As shown in Table 2, FIG. 3, and FIG. 4, the medical devices according to the present disclosure exhibited high antithrombogenicity.

In particular, it can be seen that when the repeating unit (A) is 0.6 mol % or more based on all the structural units of the copolymer, high antithrombogenicity can be obtained even under severe use conditions. Further, in the antithrombogenicity test, as a result of visual evaluation, it was found that when the repeating unit (A) was 0.9 to 4.7 mol %, particularly excellent antithrombogenicity was obtained.

In addition, Example 3 and Comparative Example 6 are copolymers obtained by combining SBAA and MEA and combining CBA and MEA, respectively. As a result of comparison, although the content (ratio) of the betaine backbone (zwitterion moiety) in the copolymer was almost equal between the two, excellent antithrombogenicity was obtained in Example 3, while the antithrombogenicity in Comparative Example 6 was poor. Therefore, it was revealed that although the copolymers obtained in Example 3 and Comparative Example 6 are both equally zwitterion-moiety-containing copolymers, when the zwitterion moiety is a SBAA-derived structure, the antithrombogenicity-improving effect is higher than in the case of CBA.

[Test 3: Blood Circulation Test Using Simulated Product Form]

The antithrombogenicity of substrates coated with the polymer (5) obtained in Example 5 and the comparative polymer (7) obtained in Comparative Example 7 was evaluated in accordance with the following method.

(Preparation of Coating Agent)

The polymer (5) and the comparative polymer (7) were each dissolved in a water-alcohol (methanol) mixed solution to a concentration of 0.05 wt % and used as a coating agent.

(Production of Medical Device)

A simulated product form (blood circulation module: the hollow fiber membrane artificial lung for external hemoperfusion according to Example 1 disclosed in JP-A-11-114056, used as an artificial lung having the structure disclosed in FIG. 4 of JP-A-2009-219936; the substrate forming the blood circulation pathway includes polypropylene, polyurethane, polycarbonate, SUS) was filled with the above coating agent from the blood import side and allowed to stand for 120 seconds. The coating agent was then removed, followed by blow drying at room temperature (25° C.) for 240 minutes.

(Evaluation)

The above blood circulation module was connected to a blood reservoir using a connection tube (made of flexible polyvinyl chloride, about 100 cm in overall length×8 mm in inner diameter) and thereby incorporated into an extracorporeal circulation circuit. Subsequently, the extracorporeal circulation circuit was filled with 200 ml of Ringer's lactate, and then 200 ml of heparin-added human fresh blood was added. The heparin concentration in the circulating blood was set at 0.5 units/ml. Circulation was performed at room temperature (25° C.), 500 ml/min. After 120 minutes from the start of circulation, the blood was sampled from each blood circulation circuit, and the thrombin-antithrombin complex (TAT) concentration, which is an index of the activation of the blood coagulation system, was measured. The TAT concentration was measured using a measurement kit by EIA method. A high TAT concentration indicates an activated state of coagulation, where it can be said that thrombus formation is likely to occur.

TABLE 3

| | TAT Concentration [ng/ml] |
|---|---|
| Coated with Polymer (5) of Example 5 | 180 |
| Coated with Comparative Polymer (7) of Comparative Example 7 | 2640 |

In the blood circulation module coated with the copolymer (5) of Example 5, the TAT concentration was lower than in the blood circulation module coated with the comparative polymer (7) of Comparative Example 7. That is, it was confirmed that in the medical device according to the present disclosure, the activation of the blood coagulation system is low, indicating excellent antithrombogenicity.

From above, it can be seen that the medical device according to the present disclosure exhibits excellent antithrombogenicity even when used under severe conditions prone to thrombus formation, as in the case of a medical device having a constricted portion such as a tube joint, for example, where steps are present on the surface that contacts blood.

The detailed description above describes a medical material and a medical device using the medical material representing examples of the inventive medical material and medical device disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical material comprising a copolymer having:
   a repeating unit (A) represented by the following formula (1):

[Chemical Formula 1]

(1)

wherein $R^{11}$ is a hydrogen atom or a methyl group, Z is an oxygen atom or —NH—, $R^{12}$ is a $C^{1-6}$ alkylene group, $R^{13}$ and $R^{14}$ are each independently a $C_{1-4}$ alkyl group, and R15 is a $C_{1-6}$ alkylene group; and
a repeating unit (B) represented by the following formula (2):

[Chemical Formula 2]

(2)

wherein $R^{21}$ is a hydrogen atom or a methyl group, $R^{22}$ is a $C_{1-6}$ alkylene group, and $R^{23}$ is a $C_{1-4}$ alkyl group, the repeating unit (A) being contained in a proportion of 0.6 to 7 mol % based on all the structural units of the copolymer.

2. The medical material according to claim 1, wherein in the formula (2), $R^{21}$ is a hydrogen atom or a methyl group, $R^{22}$ is a $C_{1-3}$ alkylene group, and $R^{23}$ is a $C_{1-2}$ alkyl group.

3. The medical material according to claim 1, wherein in the formula (1), $R^{11}$ is a methyl group, Z is an oxygen atom or —NH—, $R^{12}$ is a $C_{1-4}$ alkylene group, $R^{13}$ and $R^{14}$ are each independently a $C_{1-2}$ alkyl group, and $R^{15}$ is a $C_{1-4}$ alkylene group.

4. The medical material according to claim 1, wherein the copolymer includes 0.6 to 7 mol % the repeating unit (A) and 99.4 to 93 mol % the repeating unit (B) (the total amount of the repeating unit (A) and the repeating unit (B) is 100 mol %).

5. A medical device comprising:
a substrate; and,
on a surface of the substrate, a coating layer containing the medical material according to claim 1.

6. The medical device according to claim 5, wherein the coating layer containing the medical material is coated on a lumenal surface of the medical device.

7. The medical material according to claim 1, wherein the repeating unit (A) is selected from the group consisting of [2-(methacryloyloxy)ethyl]dimethyl-(3-sulfopropyl)ammonium hydroxide, [2-(acryloyloxy)ethyl]dimethyl-(3-sulfopropyl)ammonium hydroxide, {2-[(meth)acryloyloxy]ethyl}dimethyl-(2-sulfoethyl)ammonium hydroxide, {2-[(meth)acryloyloxy]ethyl}diethyl-(2-sulfoethyl)ammonium hydroxide, {2-[(meth)acryloyloxy]ethyl}diethyl-(3-sulfopropyl)ammonium hydroxide, {3-[(meth)acryloyloxy]propyl}dimethyl-(2-sulfoethyl)ammonium hydroxide, {3-[(meth)acryloyloxy]propyl}dimethyl-(3-sulfopropyl) ammonium hydroxide, {3-[(meth)acryloyloxy]propyl}diethyl-(2-sulfoethyl)ammonium hydroxide, {3-[(meth)acryloyloxy]propyl}diethyl-(3-sulfopropyl) ammonium hydroxide, [3-(methacryloylamino)propyl]dimethyl(3-sulfopropyl)ammonium hydroxide, [3-(acryloylamino)propyl]dimethyl(3-sulfopropyl)ammonium hydroxide, {2-[(meth)acryloylamino]ethyl}dimethyl(2-sulfoethyl)ammonium hydroxide, {2-[(meth)acryloylamino]ethyl}dimethyl(3-sulfopropyl)ammonium hydroxide, {2-[(meth)acryloylamino]ethyl}diethyl(2-sulfoethyl) ammonium hydroxide, {2-[(meth)acryloylamino]ethyl}diethyl(3-sulfopropyl)ammonium hydroxide, {3-[(meth)acryloylamino]propyl}dimethyl(2-sulfoethyl) ammonium hydroxide, {3-[(meth)acryloylamino]propyl}diethyl(2-sulfoethyl)ammonium hydroxide, {3-[(meth)acryloylamino]propyl}diethyl(3-sulfopropyl) ammonium hydroxide and combinations thereof.

8. The medical material according to claim 1, wherein the repeating unit (B) is selected from the group consisting of methoxymethyl acrylate, methoxyethyl acrylate (MEA), methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate.

9. The medical material according to claim 1, wherein the medical material further comprises a repeating unit selected from the group consisting of acrylamide, N, N-dimethylacrylamide, N, N-diethylacrylamide, aminomethyl acrylate, aminoethyl acrylate, aminoisopropyl acrylate, diaminomethyl acrylate, diaminoethyl acrylate, diaminobutyl acrylate, methacrylamide, N,N-dimethylmethacrylamide, N,N-diethylmethacrylamide, aminomethyl methacrylate, aminoethyl methacrylate, diaminomethyl methacrylate, diaminoethyl methacrylate, methyl acrylate, ethyl acrylate, isopropyl acrylate, butyl acrylate, 2-ethylhexyl acrylate, methyl methacrylate, ethyl methacrylate, butyl methacrylate, hexyl acrylate, hexyl methacrylate, ethylene, propylene, N-vinylacetamide, N-isopropenylacetamide, N-(meth)acryloylmorpholine and combinations thereof.

10. A medical device comprising the medical material according to claim 1,
wherein the medical device comprises a stepped tube, and the medical material is coated on a lumenal surface of the stepped tube.

11. The medical device of claim 10, wherein the medical device is selected from the group consisting of implantable prostheses, treating instruments, artifical organs, catheters and guidewires.

12. The medical device according to claim 10, wherein the medical device is a catheter or a guidewire.

13. The medical material according to claim 1, wherein the copolymer is formed by radical polymerization, plasma polymerization, anionic polymerization or cationic polymerization.

14. The medical material according to claim 1, wherein the copolymer includes 0.8 to 6 mol % the repeating unit (A) and 99.2 to 94 mol % the repeating unit (B) (the total amount of the repeating unit (A) and the repeating unit (B) is 100 mol %).

15. The medical material according to claim 1, wherein the copolymer includes 0.9 to 4.7 mol % the repeating unit (A) and 99.1 to 95.3 mol % the repeating unit (B) (the total amount of the repeating unit (A) and the repeating unit (B) is 100 mol %).

16. The medical material according to claim 1, wherein the copolymer includes 1 to 4 mol % the repeating unit (A) and 99 to 96 mol % the repeating unit (B) (the total amount of the repeating unit (A) and the repeating unit (B) is 100 mol %).

17. The medical material according to claim 1, wherein the repeating unit (A) is [3-(methacryloylamino)propyl]dimethyl(3-sulfopropyl)ammonium hydroxide, wherein the repeating unit (B) is methoxyethyl acrylate (MEA), and wherein the copolymer includes 1 to 4 mol % the repeating unit (A).

\* \* \* \* \*